(12) United States Patent
Fullwood

(10) Patent No.: US 10,463,628 B2
(45) Date of Patent: Nov. 5, 2019

(54) GLYCOSAMINOGLYCAN-COATED METALLIC NANOPARTICLES AND USES THEREOF

(71) Applicant: LANCASTER UNIVERSITY BUSINESS ENTERPRISES LTD., Lancaster (GB)

(72) Inventor: Nigel James Fullwood, Lancaster (GB)

(73) Assignee: Lancaster University Business Enterprises LTD, Lancashire (GB)

(*) Notice: Subject to any disclaimer, the term of this patent is extended or adjusted under 35 U.S.C. 154(b) by 0 days.

(21) Appl. No.: 15/560,972

(22) PCT Filed: Mar. 11, 2016

(86) PCT No.: PCT/GB2016/050687
§ 371 (c)(1),
(2) Date: Sep. 22, 2017

(87) PCT Pub. No.: WO2016/156788
PCT Pub. Date: Oct. 6, 2016

(65) Prior Publication Data
US 2018/0049992 A1   Feb. 22, 2018

(30) Foreign Application Priority Data

Mar. 31, 2015 (GB) .................................. 1505520.5

(51) Int. Cl.
| | |
|---|---|
| *A61K 9/51* | (2006.01) |
| *A61K 33/24* | (2019.01) |
| *A61K 33/38* | (2006.01) |
| *A61K 8/73* | (2006.01) |
| *A61Q 19/08* | (2006.01) |
| *A61K 9/00* | (2006.01) |
| *A61K 8/19* | (2006.01) |
| *A61K 31/728* | (2006.01) |
| *A61K 33/00* | (2006.01) |
| *A61K 47/65* | (2017.01) |
| *A61K 47/68* | (2017.01) |
| *A61K 47/69* | (2017.01) |

(52) U.S. Cl.
CPC .............. *A61K 9/5161* (2013.01); *A61K 8/19* (2013.01); *A61K 8/73* (2013.01); *A61K 8/735* (2013.01); *A61K 9/0048* (2013.01); *A61K 9/5169* (2013.01); *A61K 31/728* (2013.01); *A61K 33/00* (2013.01); *A61K 33/24* (2013.01); *A61K 33/38* (2013.01); *A61K 47/65* (2017.08); *A61K 47/68* (2017.08); *A61K 47/6923* (2017.08); *A61K 47/6925* (2017.08); *A61K 47/6929* (2017.08); *A61Q 19/08* (2013.01); *A61K 2800/412* (2013.01); *A61K 2800/413* (2013.01); *A61K 2800/624* (2013.01); *A61K 2800/651* (2013.01); *A61K 2800/654* (2013.01)

(58) Field of Classification Search
CPC ..... A61K 9/5161; A61K 9/0048; A61K 33/38
See application file for complete search history.

(56) References Cited

U.S. PATENT DOCUMENTS 8,901,080 B2 * 12/2014 Castelltort ............... A61K 8/02
514/18.8
2010/0248260 A1 * 9/2010 Ban ....................... A61K 33/24
435/7.1

FOREIGN PATENT DOCUMENTS

| EP | 2228393 A1 | 9/2010 |
| WO | 2009075774 A2 | 6/2009 |
| WO | 2012089768 A1 | 7/2012 |

OTHER PUBLICATIONS

Erika Soderstjerna et al: "Silver and Gold Nanoparticles Exposure to In Vitro Cultured Retina—Studies on Nanoparticle Internalization, Apoptosis, Oxidative Stress, Glial- and Microglial Activity", Plos One Aug. 21, 2014, vol. 9 No. 8, e105359, 16 pages.
International Search Report and Written Opinion issued in PCT/GB2016/050687, dated May 23, 2016 15 pages.
Lee H et al: Synthesis, Characterization, and In Vivo Diagnostic Applications of Hyaluronic Acid Imnobilized Gold Nanoprobes: Biomaterials, Elsevier Science Publishers BV., Barking, GB, vol. 29, No. 35, Dec. 1, 2008 (Dec. 1, 2008), pp. 4709-4718.
Liesje Sintubin et al: "Biologically Produced Nanosilver: Current State and Future Perspectives" Biotechnology and Bioengineering, vol. 109, No. 10 Jun. 27, 2012 (Jun. 27, 2012), Oct. 27, 2012 (Oct. 27, 2012), pp. 2422-2436.
Suvarna P. Phadatare et al: "A Comprehensive Review on Dry Eye Disease: Diagnosis, Medical Management, Recent Developments, and Future Challenges" Advances in Pharmaceutics, vol. 2015, Jan. 1, 2015 (Jan. 1, 2015), 12 pages.

* cited by examiner

*Primary Examiner* — Kyle A Purdy
(74) *Attorney, Agent, or Firm* — Faegre Baker Daniels LLP

(57) ABSTRACT

The present invention is a composition comprising a plurality of nanoparticles of at least one noble metal each coated with a plurality of linker molecules, at least some of which are attached to at least one of a plurality of glycosaminoglycan chains.

17 Claims, 1 Drawing Sheet

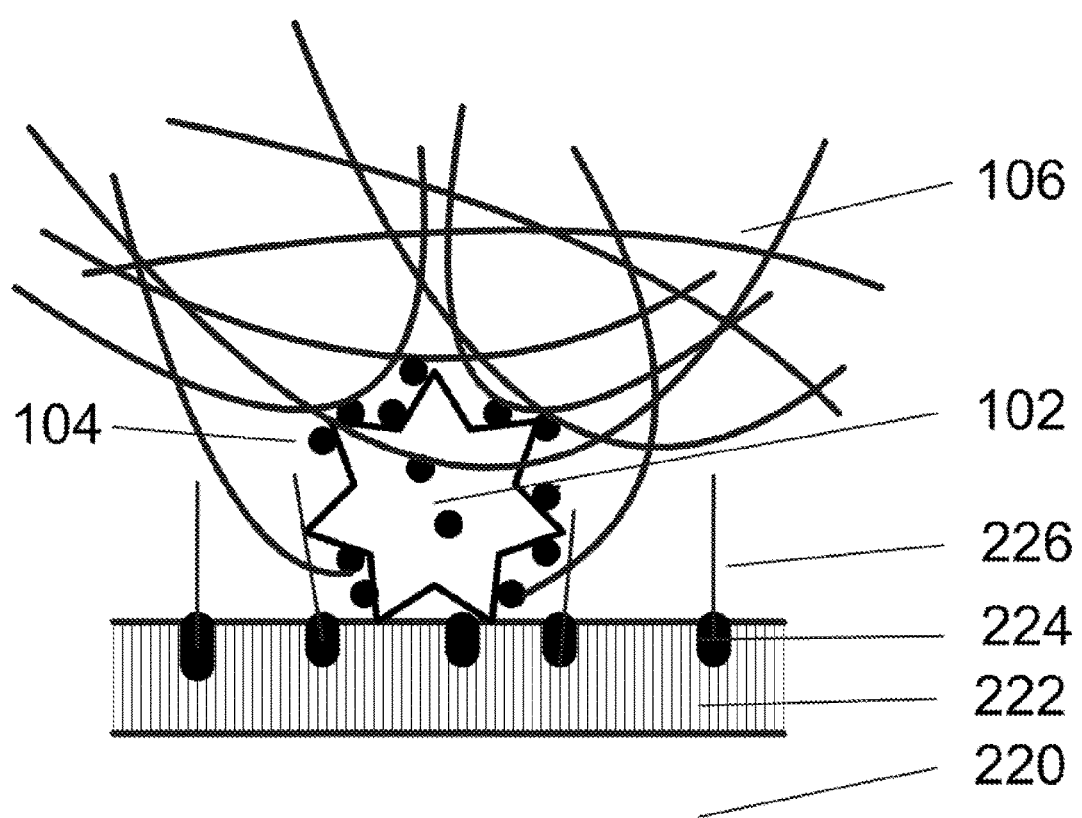

GLYCOSAMINOGLYCAN-COATED METALLIC NANOPARTICLES AND USES THEREOF

The present invention concerns the treatment of the symptoms of conditions involving lack of hydration in surface cells. One example is the treatment or prevention of dry eye (a plurality of conditions including for example keratoconjunctivitis sicca). A further example is the treatment or prevention of dry or wrinkled skin.

By treatment is meant a beneficial outcome for the patient. This may comprise a substantial improvement or simply some degree of amelioration.

Dry eye may be caused by inadequate tear production and/or instability of the tear film on the surface of the eye. Almost all populations around the world are affected by dry eye, and almost every individual experiences some form of dry eye discomfort during their lifetime, particularly in old age. Some occurrences are chronic and some are mild. Dry eye can be painful and irritating for sufferers.

There are some treatments currently available for the symptoms of dry eye. The simplest comprises distilled water. Slightly saline water is also used. Such preparations may be available over-the-counter in pharmacies as "artificial tears". They may contain water, salts and polymers such as cellulose derivatives.

Glycosaminoglycans (GAGs) have also been used to treat dry eye. GAGs are long unbranched polysaccharides consisting of a repeating disaccharide unit. There are four classes of GAGs: Heparin/heparan sulphate GAGs, chondroitin/dermatan sulphate GAGs, Keratan sulphate GAGs and fourthly hyaluronic acid (also known as hyaluronan or HA).

HA is a negatively charged anionic non-sulphated glycosaminoglycan. It is found naturally in the human body in connective, epithelial and neural tissues including the eye and skin. Molecules of glycosaminoglycan (such as HA) may be very long chains with molecular weights over one million. In combination with water, these long chains may form a highly hydrated gel-like substance which effects hydration of adjacent tissue.

Known treatments may help hydrate the eye and stabilise the tear film but they have the disadvantage that they remain on the eye for only a short time before being washed away, and require frequent re-application.

Dry wrinkled skin may be the result of a medical condition, such as xeroderma, and/or may be a natural result of old age and/or exposure to sun and wind. Certain topical products may also dehydrate skin. Treatments for the symptoms (and for prevention) are available, typically ointments comprising creams and emulsions. Glycosaminoglycans such as HA are known for use in such treatments.

It is one objective of the present invention to overcome the disadvantages of current approaches to the treatment and prevention of such conditions whether or not stated explicitly here.

The problem to be solved is to invent a preparation which treats and/or prevents the symptoms of such conditions, remains on the tissue surface and is suitable for regulatory approval.

The present invention is a composition comprising a plurality of nanoparticles of at least one noble metal each coated with a plurality of linker molecules, at least some of which are attached to at least one of a plurality of glycosaminoglycan chains.

In a further aspect of the present invention, there is provided a method of treating a condition which involves lack of hydration in surface cells, the method comprising:

a) administering a composition comprising a plurality of nanoparticles of at least one noble metal each coated with a plurality of linker molecules, at least some of which are attached to at least one of a plurality of glycosaminoglycan chains to a subject in need thereof.

As used herein, the term "treating" includes treating the symptoms of the condition and may relate to alleviating such symptoms e.g. reducing or preventing the occurrence of the symptoms. Reducing in this context may refer to the reduction in the severity and/or occurrence of one or more symptoms for example.

In certain embodiments, the method comprises administrating the composition topically e.g. to a surface of the subject's eye and/or skin.

In certain embodiments, the method is for the treatment of a condition selected from dry eye e.g. keratoconjunctivitis sicca and/or dry and/or wrinkled skin.

In certain embodiments, the method comprises administering approximately 0.2 milliliters per eye per day to treat dry eye. In certain embodiments, the method comprises administering e.g. applying approximately 0.2 milliliters per square centimeter to the subject's skin for the treatment of dry and/or wrinkled skin. Skilled persons will recognise that the required quantity may vary from person to person and between conditions.

At least some of the nanoparticles may comprise silver or gold, and at least some of the nanoparticles may have an angular geometry. The maximum dimension of the nanoparticles may be 250 nanometers or less; 100 nanometers or less; or 10 nanometers or less.

The linker may be aggrecan or HAPLN1 and/or an antibody. The glycosaminoglycan may comprise hyaluronic acid and/or derivatives thereof The composition may be formulated as a topical product, for example for the treatment and/or prevention of symptoms of dry eye (for example keratoconjunctivitis sicca), dry and/or wrinkled skin and/or as a component in medical and/or cosmetic products.

FIG. 1 shows schematically the components of certain embodiments of the present invention and their interaction with the surface of a cell (for example a corneal cell or a skin cell). In order to enhance clarity of exposition, FIG. 1 is not drawn to scale and the shapes and sizes of the component parts are simplified and adjusted for clarity.

FIG. 1 shows a nanoparticle (102) adhering to a cell membrane (222). Each nanoparticle (102) is coated with linker molecules (104) which in turn bind to glycosaminoglycan chains (106). The nanoparticles (102) may have any suitable size. Embodiments may contain nanoparticles (102) whose maximum dimension does not exceed 250 nm, 200 nm, 150 nm, 100 nm, 50 nm, 25 nm, 10 nm or any other suitable size.

In more detail, the cell body (220) is enclosed by the cell membrane (222). There are membrane proteins and lipids (224) to which are attached carbohydrate chains (226). It is these chains (226) and the glycocalyx (a layer of mostly glycolipids and glycoproteins on the surface of the membrane (222)) to which the nanoparticles (102) attach.

The noble metal nanoparticles (102) provide enhanced adhesion to cells for the glycosaminoglycan chains (106). The nanoparticles (102) may be of any suitable geometry for example a rounded shape, but are preferably angular with convexities and concavities, for example star-shaped. The larger surface area of an angular nanoparticle (102) may further increase its adhesive interaction with the glycocalyx.

Suitable noble metals may comprise ruthenium, rhodium, palladium, silver, iridium, platinum and gold.

Different embodiments of the present invention may be applicable for the treatment and/or prevention of different conditions.

Glycosaminoglycans (106) such as HA bind strongly to a range of molecules (linkers (104)) including aggrecan, link protein HAPLN1 or antibodies.

A suitable antibody to act as linker (104) is an antibody raised against the respective glycosaminoglycan (106), so that its epitope is part of the respective glycosaminoglycan (106). Such antibodies (104) may be monoclonal or polyclonal. A first suitable example is a monoclonal anti-chondroitin sulphate antibody (Sigma Aldrich product number C8035). A second suitable example is an anti-hyaluronic acid antibody (Abcam® product number ab93321). Those skilled in the art will be aware of and/or be able to source other suitable antibodies.

In general, nanoparticles (102) are first coated with linker molecules (104). This may use a method that adjusts the isoelectric point of the linker (104) and the surface charge of the nanoparticle (102) through salt concentration and controlled sonication. The resulting nanoparticle (102) coated with linker (104) is then mixed with glycosaminoglycan (106). The glycosaminoglycan chains (106) then attach (laterally or terminally) to the linker (104) and in combination with water may form hydrated complexes.

The following paragraphs detail the manufacture of a first embodiment of the present invention using aggrecan (also known as cartilage-specific proteoglycan core protein (CSPCP)) as the linker (104) and HA as the glycosaminoglycan (106):

The starting material is an aqueous solution of 0.02 mg/ml colloidal silver nanoparticles (102) (Sigma Aldrich catalogue number 730777-25ML) to which is added 10 µg/ml of aggrecan molecules (104) (Sigma Aldrich catalogue number A1960). The pH is adjusted to 5.4 with 0.1 M sodium hydroxide solution, and binding then occurs between the nanoparticle (102) and aggrecan (104).

There are then applied five second bursts of sonication repeated once per minute over a 30 minute period. This dislodges poorly bound linker (104) and breaks up clumps of linker (104) giving a more even distribution of the linker (104) over the nanoparticle (102).

The aggrecan/nanoparticle conjugate is mixed at a ratio of 1 to 10 with a 0.15% solution of sodium hyaluronan (106) (R and D Systems catalogue number GLR002). This solution is then buffered with 0.02 M sodium citrate buffer until a pH of 7.0 is achieved.

This embodiment is preferably formulated for dispensing in individual 0.25 milliliter vials which are sterile until used and then discarded. Alternatively the solution may be supplied in larger amounts via the use of a preservative. A suitable preservative is 0.001% benzalkonium chloride.

The following paragraphs detail the manufacture of a second embodiment of the present invention using HAPLN1 as the linker (104) and HA as the glycosaminoglycan (106):

The starting material is an aqueous solution of 0.02 mg/ml colloidal silver nanoparticles (102) (Sigma Aldrich catalogue number 730777-25ML) to which is added 1 µg/ml of HAPLN1 (104) (MyBioSource catalogue number MBS953767). The pH is adjusted to 5.6 with 0.1 M sodium hydroxide, and binding then occurs between the nanoparticle (102) and HAPLN1 linker (104).

Sonication is then applied as described above for the first embodiment.

The HAPLN1/nanoparticle conjugate is mixed at a ratio of 1 to 10 with a 0.15% solution of sodium hyaluronan (106) (R and D Systems catalogue number GLR002). This solution is then buffered with a 0.02 M sodium citrate buffer to a pH of 7.0

The second embodiment is preferably dispensed and/or supplied as described above for the first embodiment.

The following paragraphs detail the manufacture of a third embodiment of the present invention using an antibody as the linker (104) and HA as the glycosaminoglycan (106):

The starting material is an aqueous solution of 0.02 mg/ml colloidal silver nanoparticles (102) (Sigma Aldrich catalogue number 730777-25ML) to which is added 5 µg/ml of anti-HA IgG polyclonal antibody (Abcam® catalogue number ab93321). The pH is adjusted to 6.0 with 0.1 M sodium hydroxide, and binding then occurs between the nanoparticle (102) and antibody (104).

Sonication is then applied as described above for the first embodiment.

The antibody/nanoparticle conjugate is mixed at a ratio of 1 to 10 with a 0.15% solution of sodium hyaluronan (106) (R and D Systems catalogue number GLR002). This solution is then buffered with a 0.02 M sodium citrate buffer to a pH of 7.0

The third embodiment is preferably dispensed and/or supplied as described above for the first embodiment.

Advantageously some of the components of the present invention are non-toxic, naturally found in the human body and/or already in use in contemporary medicine. Colloidal metals (for example gold and silver) are currently available as a health supplement (for ingestion) and silver solutions have been used on the human eye for many decades. Dressings treated with silver are used to reduce skin infection. HA solution (without nanoparticles (102) and without linker (104)) is currently considered the "gold standard" for the treatment of dry eye by Moorfields Hospital in London.

When using one of the above embodiments, a typical patient may use approximately 0.2 milliliters per eye per day, and approximately 0.2 milliliters per square centimeter for application to skin. Skilled persons will recognise that the required quantity may vary from person to person and between conditions.

In use, the nanoparticles (102) serve to anchor the glycosaminoglycan (106) to the cells (220) thus providing a hydrated layer above the surface of the cell (220). This additional hydration may serve to prevent and/or ease symptoms (for example in dry eye) and/or increase the interaction of the glycosaminoglycan (106) with the cell (220) (for example with regard to dry skin).

In use for dry eye the composition attaches to the cell membrane (222) via the surface charge on the metallic nanoparticles (102). The glycosaminoglycan chains (106) interact forming a highly hydrated network, stabilising the base of the tear film and lubricating the surface of the eye (222) during blinking.

The composition of the present invention may suitably be used as a component of a wide range of preparations, for example medical products and/or cosmetic products where skin hydration is desired.

While the present invention has been described in terms of several embodiments, those persons skilled in the art will recognise that the present invention is not limited to the embodiments and examples described, but can be practised with modification and alteration within the scope of the appended claims. The Description is thus to be regarded as illustrative instead of limiting.

The invention claimed is:

1. A method of treating symptoms of dry eye conditions, comprising administering a composition comprising a plurality of nanoparticles of at least one noble metal each coated with a plurality of linker molecules, at least some of which are attached to at least one of a plurality of glycosaminoglycan chains.

2. The method of claim 1 where at least some nanoparticles comprise silver.

3. The method of claim 1 where at least some nanoparticles comprise gold.

4. The method as in claim 1 where at least some nanoparticles comprise an angular geometry.

5. The method of claim 1 where the maximum dimension of the nanoparticles does not exceed 250 nanometers.

6. The method of claim 1 where the maximum dimension of the nanoparticles does not exceed 100 nanometers.

7. The method of claim 1 where the maximum dimension of the nanoparticles does not exceed 10 nanometers.

8. The method of claim 1 where the linker is aggrecan.

9. The method of claim 1 where the linker is HAPLN1.

10. The method of claim 1 where the linker is an antibody.

11. The method of claim 1 where the glycosaminoglycan chains comprise hyaluronic acid and/or derivatives thereof.

12. The method of claim 1 wherein the composition is formulated as a topical treatment.

13. The method of claim 1, wherein the dry eye condition comprises keratoconjunctivitis sicca.

14. The method of claim 1, where the method comprises administering approximately 0.2 milliliters of the composition per eye per day.

15. A method of treating a condition which involves lack of hydration in surface cells, comprising administering a composition comprising a plurality of nanoparticles of at least one noble metal each coated with a plurality of linker molecules, at least some of which are attached to at least one of a plurality of glycosaminoglycan chains, to a surface of a subject's eye.

16. The method of claim 15, wherein the condition is a dry eye condition.

17. The method of claim 15, wherein approximately 0.2 milliliters of the composition are administered per eye per day.

* * * * *